(12) United States Patent
Bryzek et al.

(10) Patent No.: US 10,966,683 B2
(45) Date of Patent: Apr. 6, 2021

(54) INTEGRATED ULTRASONIC TRANSDUCERS

(71) Applicant: EXO IMAGING INC., Oakland, CA (US)

(72) Inventors: Janusz Bryzek, Oakland, CA (US); Sandeep Akkaraju, Wellesley, MA (US); Yusuf Haque, Woodside, CA (US); Joe Adam, Truckee, CA (US)

(73) Assignee: EXO IMAGING INC., Redwood City, CA (US)

( * ) Notice: Subject to any disclaimer, the term of this patent is extended or adjusted under 35 U.S.C. 154(b) by 553 days.

(21) Appl. No.: 15/933,309

(22) Filed: Mar. 22, 2018

(65) Prior Publication Data
US 2019/0290243 A1 Sep. 26, 2019

(51) Int. Cl.
*B06B 1/06* (2006.01)
*A61B 8/00* (2006.01)
(Continued)

(52) U.S. Cl.
CPC .......... *A61B 8/4494* (2013.01); *A61B 8/4488* (2013.01); *B06B 1/0215* (2013.01); *B06B 1/067* (2013.01); *B06B 1/0622* (2013.01); *B06B 1/0666* (2013.01); *B06B 1/0681* (2013.01); *B81B 7/0058* (2013.01); *G01S 15/8938* (2013.01); *G01S 15/8965* (2013.01); *H01L 24/32* (2013.01); *H01L 24/48* (2013.01); *H01L 24/73* (2013.01); *B06B 2201/76* (2013.01); *B81B 2207/012* (2013.01); *B81B 2207/053* (2013.01); *B81B 2207/098* (2013.01); *H01L 2224/16145* (2013.01); *H01L 2224/32225* (2013.01);
(Continued)

(58) Field of Classification Search
CPC ..... B06B 1/0622; B06B 1/0666; B06B 1/067; B06B 1/0681
See application file for complete search history.

(56) References Cited

U.S. PATENT DOCUMENTS 6,159,149 A * 12/2000 Erikson ................ A61B 8/4483
  600/437
2002/0000646 A1   1/2002 Gooch et al.
(Continued)

FOREIGN PATENT DOCUMENTS

WO   WO-2017065691 A1   4/2017
WO   WO-2018112042 A1   6/2018
(Continued)

OTHER PUBLICATIONS

PCT/US2019/021500 International Search Report and Written Opinion dated May 24, 2019.
(Continued)

*Primary Examiner* — Derek J Rosenau
(74) *Attorney, Agent, or Firm* — Wilson Sonsini Goodrich & Rosati (57) ABSTRACT

A transducer assembly includes: a microelectromechanical systems (MEMS) die including a plurality of piezoelectric elements; a complementary metal-oxide-semiconductor (CMOS) die electrically coupled to the MEMS die by a first plurality of bumps and including at least one circuit for controlling the plurality of piezoelectric elements; and a package secured to the CMOS die by an adhesive layer and electrically connected to the CMOS die.

57 Claims, 8 Drawing Sheets

(51) Int. Cl.
    *H01L 23/00*     (2006.01)
    *B06B 1/02*     (2006.01)
    *G01S 15/89*     (2006.01)
    *B81B 7/00*     (2006.01)

(52) U.S. Cl.
    CPC ............... *H01L 2224/48225* (2013.01); *H01L 2224/73207* (2013.01); *H01L 2224/73253* (2013.01); *H01L 2224/73265* (2013.01); *H01L 2924/1461* (2013.01)

(56) References Cited

U.S. PATENT DOCUMENTS

| | | | |
|---|---|---|---|
| 2007/0040477 A1* | 2/2007 | Sugiura | G01S 7/521 310/324 |
| 2007/0157731 A1 | 7/2007 | Okuda et al. | |
| 2009/0048519 A1 | 2/2009 | Hossack et al. | |
| 2009/0182233 A1 | 7/2009 | Wodnicki | |
| 2012/0150038 A1 | 6/2012 | Osawa | |
| 2015/0276685 A1 | 10/2015 | Yasuhara et al. | |
| 2016/0041129 A1 | 2/2016 | Cho et al. | |
| 2016/0176704 A1 | 6/2016 | Cargill et al. | |
| 2016/0320426 A1 | 11/2016 | Boysel et al. | |
| 2016/0363656 A1 | 12/2016 | Angelsen | |
| 2017/0008760 A1 | 1/2017 | Lloyd et al. | |
| 2017/0043189 A1 | 2/2017 | Stoddard et al. | |
| 2017/0322292 A1 | 11/2017 | Salvia et al. | |
| 2017/0323133 A1 | 11/2017 | Tsai et al. | |
| 2018/0153510 A1 | 6/2018 | Haque et al. | |
| 2018/0153512 A1 | 6/2018 | Akkaraju et al. | |

FOREIGN PATENT DOCUMENTS

| | | |
|---|---|---|
| WO | WO-2019182771 A1 | 9/2019 |
| WO | WO-2020198257 A1 | 10/2020 |

OTHER PUBLICATIONS

PCT/US2020/024509 Invitation to Pay Additional Fees dated May 26, 2020.
PCT/US2020/024509 International Search Report and Written Opinion dated Aug. 6, 2020.

* cited by examiner

INTEGRATED ULTRASONIC TRANSDUCERS

BACKGROUND

A. Technical Field

The present invention relates to imaging devices, and more particularly, to imaging devices having a microelectromechanical systems (MEMS) die integrated to a complementary metal-oxide-semiconductor (CMOS) die/wafer.

B. Background of the Invention

A non-intrusive imaging system/probe for imaging internal organs of human body and displaying the images of the internal organs requires transmission of a signal into the human body and receiving an emitted or reflected signal from the organs. Typically, transducers that are used in an imaging system are referred to as transceivers and some of the transceivers are based on photo-acoustic or ultrasonic effects.

The conventional ultrasound probes in use for medical imaging typically use piezoelectric material, such as lead zirconate titanate (PZT) and lead magnesium niobate-lead titanate (PMN-PT) for high end imagers. Probes typically house the transducers and some other electronics with means to cause an image to be displayed on a display unit. To fabricate the conventional bulk piezoelectric elements for the transducers, one can simply cut a thick piezoelectric material slab into rectangular shaped piezoelectric elements. However, these rectangular shaped piezoelectric elements are expensive to build, since the manufacturing process involves precisely cutting of the rectangular shaped thick PZT one at a time and require a high drive voltage on the order of 200V.

Silicon based capacitive micromachined ultrasound transducers, cMUTs, emerged in late 1990s as a new tool to perform medical imaging, enabling batch fabrication of cMUTs on silicon wafers. One of the expected benefits was the potential for integration of cMUT with CMOS, as another step towards cost and power reduction. Several approaches were demonstrated for integration of cMUT with CMOS prototypes: monolithic integration, with cMUT above CMOS circuitry and cMUT adjacent to circuitry, flip-chip of MEMS and CMOS on an intermediate substrate (interposer) and flip-chip between MEMS and CMOS. However, commercial implementation of these concepts has met with a number of challenges. For instance, the conventional cMUT sensors are particularly prone to failure or drift in performance due to the charge build-up during the high voltage operation, exhibit non-linear transfer function restricting harmonic imaging and require a high drive voltage comparable to conventional probes.

Recent advances in MEMS technology made possible deposition of thin piezo films onto silicon, enabling batch fabrication of piezoelectric micromachined ultrasound transducers (pMUTs) on silicon wafers, eliminating fundamental problems of cMUTs. While cMUT requires high voltage to modulate the gap under a diaphragm to create ultrasound waves, pMUT's piezoelectric layer is used to deflect a diaphragm using much lower voltage than cMUT. pMUTs' transfer function is linear enabling harmonic imaging, and operation is not sensitive to mobile charges.

Typically, for high performance 3D imaging, a large number of pMUTs need to be integrated on a single die. In general, one or more electrical connections per pMUT elements may be needed, making wire bonding between PMUT die and CMOS die not a practical solution for low-cost 3D imagers. Furthermore, it is not desirable to have wire bonds on the human body side of pMUT, as they may pick up electromagnetic interference signals.

As such, there is a need for short connections between pMUT MEMS die and ASIC die, such as offered by the flip-chip of pMUT MEMS die on CMOS wafer or die, to enable electrical connectivity and ensure low electromagnetic interference signals.

SUMMARY OF THE DISCLOSURE

In embodiments, a transducer assembly includes: a microelectromechanical systems (MEMS) die including a plurality of piezoelectric elements; a complementary metal-oxide-semiconductor (CMOS) die electrically coupled to the MEMS die by a first plurality of bumps (or pillars) and including at least one circuit for controlling the plurality of piezoelectric elements; and a package secured to the CMOS die by an adhesive layer and electrically connected to the CMOS die. Hereinafter, the terms bump and pillar are used interchangeably.

In embodiments, an imaging device includes a transducer assembly. The transducer assembly includes: a microelectromechanical systems (MEMS) die including a plurality of piezoelectric elements; a complementary metal-oxide-semiconductor (CMOS) die electrically coupled to the MEMS die by a first plurality of bumps and including at least one circuit for controlling the plurality of piezoelectric elements; and a package secured to the CMOS die by an adhesive layer and electrically connected to the CMOS die. The plurality of piezoelectric elements generates a pressure wave, develop an electrical charge in response to a pressure wave received from outside, and generate an electrical signal corresponding to the electrical charge. The package processes the electrical signal to generate an image.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

In the following description, for purposes of explanation, specific details are set forth in order to provide an understanding of the disclosure. It will be apparent, however, to one skilled in the art that the disclosure can be practiced without these details. Furthermore, one skilled in the art will recognize that embodiments of the present disclosure, described below, may be implemented in a variety of ways, such as, an apparatus, a system, or a device.

Elements/components shown in diagrams are illustrative of exemplary embodiments of the disclosure and are meant to avoid obscuring the disclosure. Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," or "in embodiments" in various places in the specification are not necessarily all referring to the same embodiment or embodiments. The terms "include," "including," "comprise," and "comprising" shall be understood to be open terms and any lists that follow are examples and not meant to be limited to the listed items. Any headings used herein are for organizational purposes only and shall not be used to limit the scope of the description or the claims. Furthermore, the use of certain terms in various places in the specification is for illustration and should not be construed as limiting.

In embodiments, the pMUTs and transducer assemblies/packages may be used for imaging internal organs of a human/animal body as well as other therapeutic applications where ultrasonic beams are used to heat tissue for healing or focus high power ultrasonic beams for micro surgery. In embodiments, the pMUTs and transducer assemblies/packages may also be used for ultrasonic tomography applications.

In embodiments, the manufacturing cost of pMUTs may be reduced by applying modern semiconductor and wafer processing techniques. In embodiments, thin film piezoelectric layer may be spun on or sputtered onto semiconductor wafers and later patterned to create piezoelectric transducers that each have two or more electrodes. In embodiment, each piezoelectric element may be designed to have the ability to emit or receive signals at a certain frequency range. Hereinafter, the terms piezoelectric element, pMUT, sensor, transducer, transceiver, and unit pixel are used interchangeably.

Figure 1:
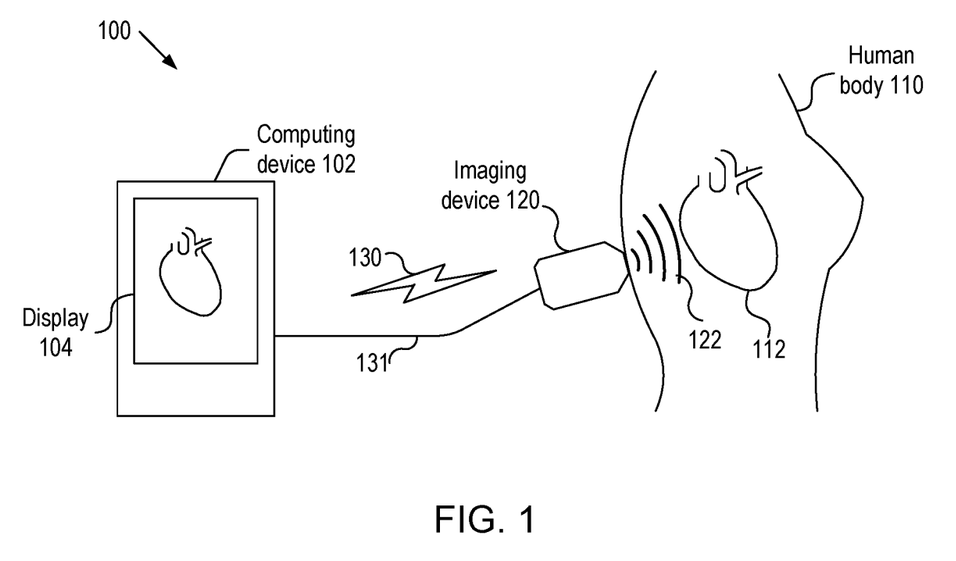
FIG. 1 shows an imaging system according to embodiments of the present disclosure.

FIG. 1 shows a schematic diagram of an imaging system 100 according to embodiments of the present disclosure. As depicted, the system 100 may include: an imaging device (or shortly imager) 120 that generates and transmits pressure waves 122 toward an internal organ 112, such as heart, in a transmit mode/process and receives pressure waves reflected from the internal organ; and a computing device (or, shortly device) 102 that sends and receives signals to the imager through a communication channel 130 and/or a cable 131. In embodiments, the internal organ 112 may reflect a portion of the pressure waves 122 toward the imager 120, and the imager 120 may capture the reflected pressure waves and generate electrical signals in a receive mode/process. The imager 120 may communicate electrical signals to the device 102 and the device 102 may display images of the organ or target on a display/screen 104 using the electrical signals.

In embodiment, the imager 120 may be used to perform one dimensional imaging, also known as A-Scan, two dimensional imaging, also known as B scan, three dimensional imaging, also sometimes referred to as C scan, four dimensional imaging, and Doppler imaging. Also, the imager may be switched to various imaging modes under program control.

In embodiments, the imager 120 may be used to get an image of internal organs of an animal, too. The imager 120 may also be used to determine direction and velocity of blood flow in arteries and veins as in Doppler mode imaging and also measure tissue stiffness. In embodiments, the pressure wave 122 may be acoustic waves that can travel through the human/animal body and be reflected by the internal organs, tissue or arteries and veins.

In embodiments, the imager 120 may be a portable device and communicate signals through the communication channel, either wirelessly 130 (using a protocol, such as 802.11 protocol) or via a cable 131 (such as USB2, USB 3, USB 3.1, USB-C, and USB thunderbolt), with the device 102. In embodiments, the device 102 may be a mobile device, such as cell phone or iPad, or a stationary computing device that can display images to a user.

In embodiments, more than one imager may be used to develop an image of the target organ. For instance, the first imager may send the pressure waves toward the target organ while the second imager may receive the pressure waves reflected from the target organ and develop electrical charges in response to the received waves.

Figure 2:
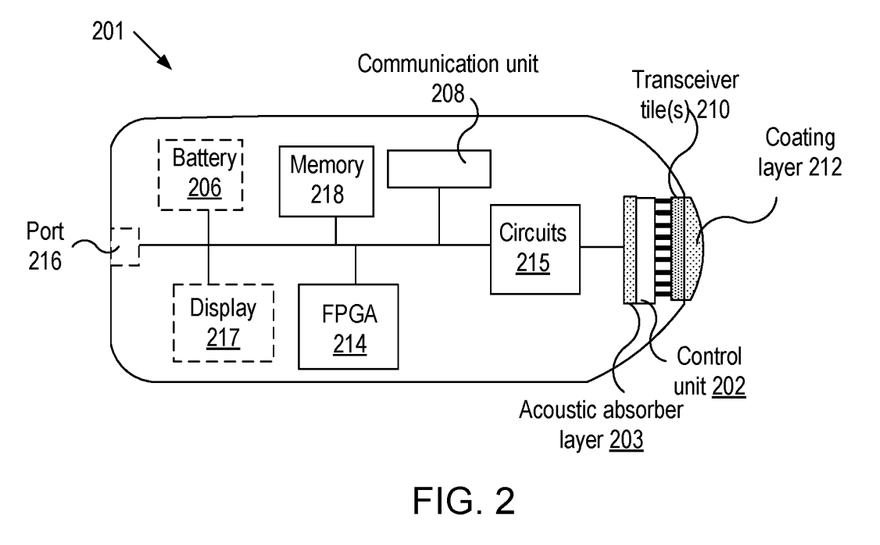
FIG. 2 shows a block diagram of an exemplary ultrasonic imager according to embodiments of the present disclosure.

FIG. 2 shows a schematic diagram of an exemplary imager 201 according to embodiments of the present disclosure. In embodiments, the imager 201 may be the same as the imager 120. It is noted that the imager 201 may have more or less than the components shown in FIG. 2.

In embodiments, the imager 201 may be an ultrasonic imager. As depicted in FIG. 2, the imager 201 may include: a transceiver tile(s) 210 for transmitting and receiving pressure waves; a coating layer 212 that operates as a lens for setting the propagation direction of and/or focusing the pressure waves and also functions as an acoustic impedance interface between the transceiver tile and the human body 110; a control unit 202, such as ASIC chip (or, shortly ASIC), for controlling the transceiver tile(s) 210 and coupled to the transducer tile 210 by bumps; Field Programmable Gate Arrays (FPGAs) 214 for controlling the components of the imager 201; a circuit(s) 215, such as Analogue Front End (AFE), for processing/conditioning signals;

an acoustic absorber layer 203 for absorbing waves that are generated by the transducer tiles 210 and propagate toward the circuit 215; a communication unit 208 for communicating data with an external device, such as the device 102, through one or more ports 216; a memory 218 for storing data; a battery 206 for providing electrical power to the components of the imager; and optionally a display 217 for displaying images of the target organs.

In embodiments, the device 102 may have a display/screen. In such a case, the display may not be included in the imager 201. In embodiments, the imager 201 may receive electrical power from the device 102 through one of the ports 216. In such a case, the imager 201 may not include the battery 206. It is noted that one or more of the components of the imager 201 may be combined into one integral electrical element. Likewise, each component of the imager 201 may be implemented in one or more electrical elements.

In embodiments, the user may apply gel on the skin of the human body 110 before the body 110 makes a direct contact with the coating layer 212 so that the impedance matching at the interface between the coating layer 212 and the human body 110 may be improved, i.e., the loss of the pressure wave 122 at the interface is reduced and the loss of the reflected wave travelling toward the imager 201 is also reduced at the interface. In embodiments, the transceiver tiles 210 may be mounted on a substrate and may be attached to an acoustic absorber layer. This layer absorbs any ultrasonic signals that are emitted in the reverse direction, which may otherwise be reflected and interfere with the quality of the image.

As discussed below, the coating layer 212 may be only a flat matching layer just to maximize transmission of acoustic signals from the transducer to the body and vice versa. Beam focus is not required in this case, because it can be electronically implemented in control unit 202. The imager 201 may use the reflected signal to create an image of the organ 112 and results may be displayed on a screen in a variety of format, such as graphs, plots, and statistics shown with or without the images of the organ 112.

In embodiments, the control unit 202, such as ASIC, may be assembled as one unit together with the transceiver tiles. In other embodiments, the control unit 202 may be located outside the imager 120 and electrically coupled to the transceiver tile 210 via a cable. In embodiments, the imager 201 may include a housing that encloses the components 202-215 and a heat dissipation mechanism for dissipating heat energy generated by the components.

Figure 3:
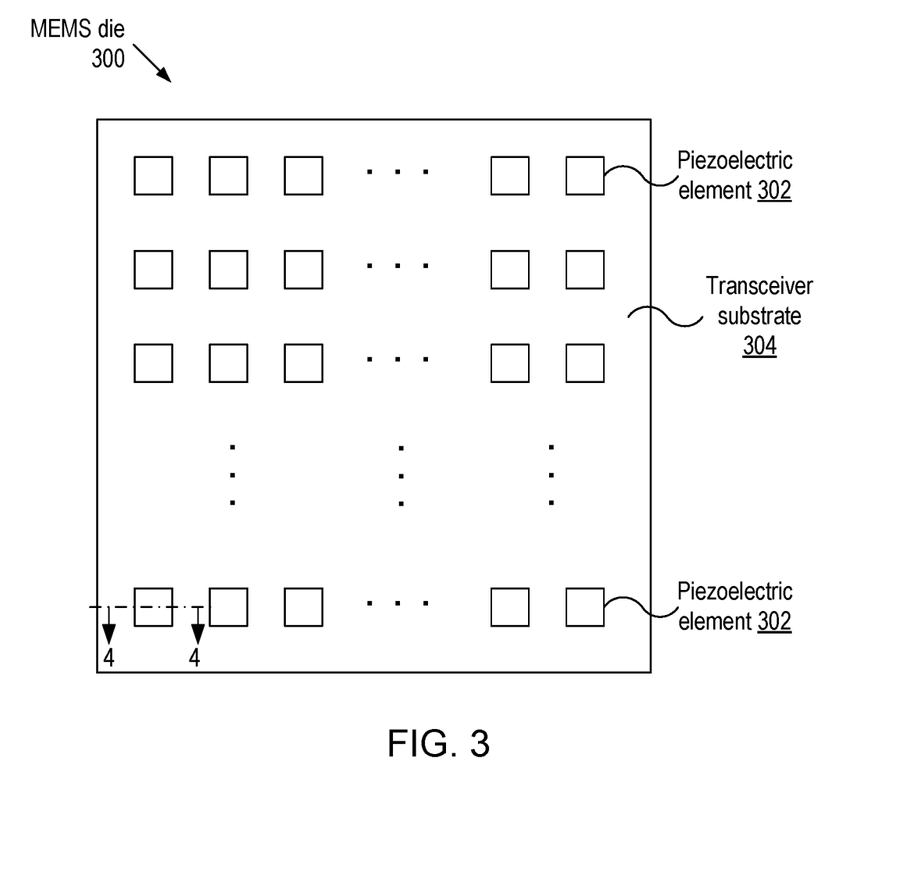
FIG. 3 shows a simplified top view of an exemplary MEM die according to embodiments of the present disclosure.

FIG. 3 shows a top view of an exemplary MEMS die 300 included in the MEMS package 210 according to embodiments of the present disclosure. As depicted, the MEMS die 300 may include a transceiver substrate 304 and one or more piezoelectric elements (or pMUTs) 302 arranged in one dimensional array or two dimensional array on the transceiver substrate 304.

Unlike the conventional systems that use bulk piezoelectric elements, in embodiments, the pMUTs 302 may be formed on a wafer and the wafer may be diced to form the MEMS die 300. This process may reduce the manufacturing cost since the MEMS die 300 may be fabricated in high volume and at low cost. In embodiments, the diameter of the wafer may range 6~12 inches and many pMUT arrays may be batch manufactured on each wafer. Further, in embodiments, as discussed below, the integrated circuits for controlling the pMUTs 302 may be formed in a CMOS wafer/die (such as an ASIC chip) so that the pMUTs 302 may be connected to the matching integrated circuits in close proximity, preferably within 25 µm-100 µm. In embodiments, a Bipolar Complementary Metal Oxide Semiconductor (BICMOS) or any other suitable process may be used instead of CMOS wafer/die.

In embodiments, the projection area of each piezoelectric element 302 may have any suitable shape such as, square, rectangle, and circle, so on. In embodiments, two or more piezoelectric elements may be connected to form a larger pixel element. In embodiments, the two dimensional array of piezoelectric elements 302 may be arranged in orthogonal directions. In embodiments, to create a line element, a column of N piezoelectric elements 302 may be connected electrically in parallel. Then, this line element may provide transmission and reception of ultrasonic signals similar to those achieved by a continuous piezoelectric element that is about N times longer than each element.

To mimic a line element of the conventional designs, the shape of a piezoelectric element of a given width may need to be very tall. For example, a line element of a conventional design may be 280 µm in width and 8000 µm tall, while the thickness may be 100 µm. However, on the MEMS die 300, it is advantageous to design a line element using a plurality of identical piezoelectric elements 302, where each element may have its characteristic center frequency. In embodiments, when a plurality of the piezoelectric elements 302 are connected together, the composite structure (i.e. the line element) may act as one line element with a center frequency that consists of the center frequencies of all the element pixels. In modern semiconductor processes, these center frequencies match well to each other and have a very small deviation from the center frequency of the line element.

In embodiments, the piezoelectric elements 302 have one or more suspended membranes that are associated with them and vibrate at a center frequency when exposed to stimulus at that frequency and behave like resonators. There is a selectivity associated with these resonators, known as a Q factor. In embodiments, for ultrasound imagers, Q may be usually designed to be low (close 1-3 or thereabouts) and achieved by a combination of design of the pixels and loading applied to the pixels in actual use. In embodiments, the loading may be provided by application of a layer of RTV/Polydimethylsiloxane (PDMS) or other matching material layers to the top face of the piezoelectric elements, where the loading may facilitate closer impedance matching between the transducer surface emitting and receiving the pressure waves and the human body part being imaged. In embodiments, the low Q and the well matched center frequency may allow the line element to essentially act like a line imaging element with substantially one center frequency.

In embodiments, for instance, each piezoelectric element 302 may be spaced 100-250 µm from each other center to center. Further to simplify, say they are square in shape. Now, let's say, to mimic a conventional line element, a column of the piezoelectric elements 302 may be connected to each other. For example, 24 piezoelectric elements 302 in a column may create a line element of roughly 8 mm in elevation, with each element being 0.25 mm in width. In embodiments, this connection may be achieved at wafer level using a metal interconnect layer, or connected in parallel using circuits in control unit 202.

For the conventional bulk piezoelectric elements, the voltage potential across the top and bottom electrodes ranges 100V~200V. For the conventional pMUTs, the voltage potential across the top and bottom electrodes could be about 10 times lower to generate the same acoustic pressure. In embodiments, in order to reduce this voltage further, the piezoelectric elements 302 may include a scaled down thin piezoelectric layer, and the piezoelectric layer may have a thickness in the order of 1 μm or less.

Figure 4:
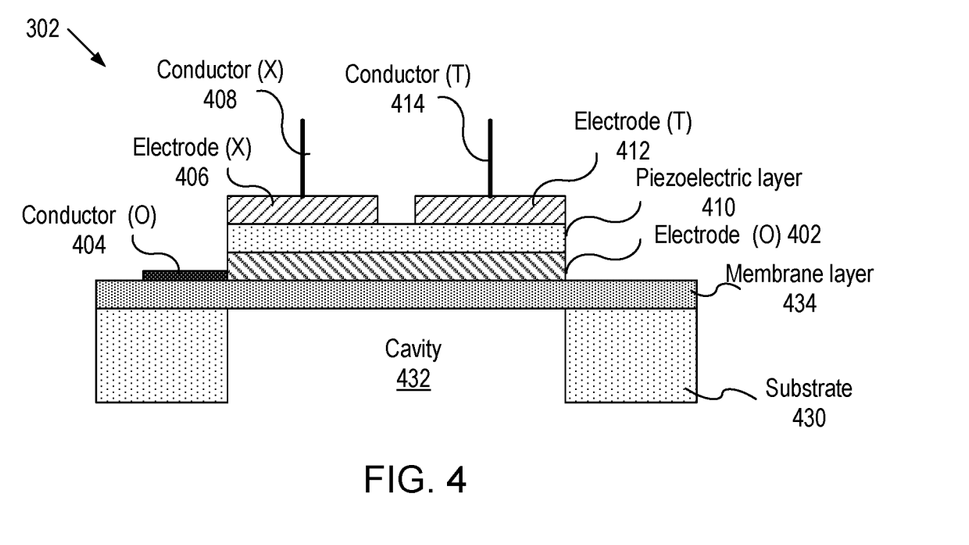
FIG. 4 shows a schematic cross sectional view of a pMUT element according to embodiments of the present disclosure.

FIG. 4 shows a schematic cross sectional diagram of the exemplary piezoelectric element 302, taken along the direction 4-4 in FIG. 3, according to embodiments of the present disclosure. As depicted, the piezoelectric element 302 may be disposed on a membrane layer 434 that is supported by a substrate 430. In embodiments, a cavity 432 may be formed in the substrate 430 to define a membrane, i.e., the substrate 430 and the membrane 434 may be formed of a monolithic body. In alternative embodiments, the membrane layer 434 may be formed by depositing SiO2 on the substrate 430. In embodiments, one or more piezoelectric elements 302 may be disposed on a membrane. In alternative embodiments, each piezoelectric element may be disposed on a separate membrane.

In embodiments, the piezoelectric element 302 may include a piezoelectric layer 410 and a first (or bottom) electrode (O) 402 that is electrically connected to a signal conductor (O) 404. In embodiments, the signal conductor (O) 404 may be formed by depositing $TiO_2$ and metal layers on the membrane layer 434. In embodiments, the piezoelectric layer 410 may be formed by the sputtering technique or by the Sol Gel process.

In embodiments, a second electrode (X) 406 may be grown above the piezoelectric layer 410 and electrically connected to a second conductor 408. A third electrode (T) 412 may be also grown above the piezoelectric layer 410 and disposed adjacent to the second conductor 412 but electrically isolated from the second conductor (X) 408. In embodiments, the second electrode (X) 406 and third electrode (T) 412 (or, equivalently, two top electrodes) may be formed by depositing one metal layer on the piezoelectric layer 410 and patterning the metal layer. In embodiments, the projection areas of the electrodes 402, 406 and 412 may have any suitable shape, such as square, rectangle, circle, and ellipse, so on.

In embodiments, the first electrode (O) 402 may be electrically connected to the conductor (O) 404 using a metal, a via and interlayer dielectrics. In embodiments, the first electrode (O) 402 may be in direct contact with the piezoelectric layer 410. The third conductor (T) 414 may be deposited or grown on the other side of the piezoelectric layer 410 with respect to the first electrode (O) 402. More information on steps for fabricating the piezoelectric element 302 may be found in a copending U.S. patent application Ser. No. 15/826,614, entitled "LOW VOLTAGE, LOW POWER MEMS TRANSDUCER WITH DIRECT INTERCONNECT CAPABILITY," filed on Nov. 29, 2017, which is herein incorporated by reference in its entirety.

While a unimorph piezoelectric element is shown in FIG. 4 purely for the purpose of illustration, in embodiments, a multiplayer piezoelectric element composed of a plurality of piezoelectric sublayers and electrodes can be utilized. In embodiments, the piezoelectric layer 410 may include at least one of PZT, KNN, PZT-N, PMN-Pt, AlN, Sc—AlN, ZnO, PVDF, and $LiNiO_3$ materials.

It is noted that a piezoelectric element of the MEMS die 300 may include other suitable number of top electrodes. For instance, the piezoelectric element may include only one top electrode (e.g. X electrode). In another example, the piezoelectric element may include more than two top electrodes. More information on the number of top electrodes and electrical connections to the top electrodes may be found in the copending U.S. patent application Ser. No. 15/826,614.

It is noted that FIG. 4 is a schematic diagram and, as such, does not illustrate the detailed structure of a piezoelectric element. For instance, an electrical pad may be disposed between one end of the conductor (X) 408 and the electrode (X) 406. Also, the MEMS die 300 may include piezoelectric elements that have different structures from the piezoelectric element 302. For instance, each piezoelectric element in the MEMS die 300 may have only one top electrode. Thus, it should be apparent to those of ordinary skill in the art that the piezoelectric element 302 is one of several types of piezoelectric elements that can be included in the MEMS die 300.

Figure 5A:
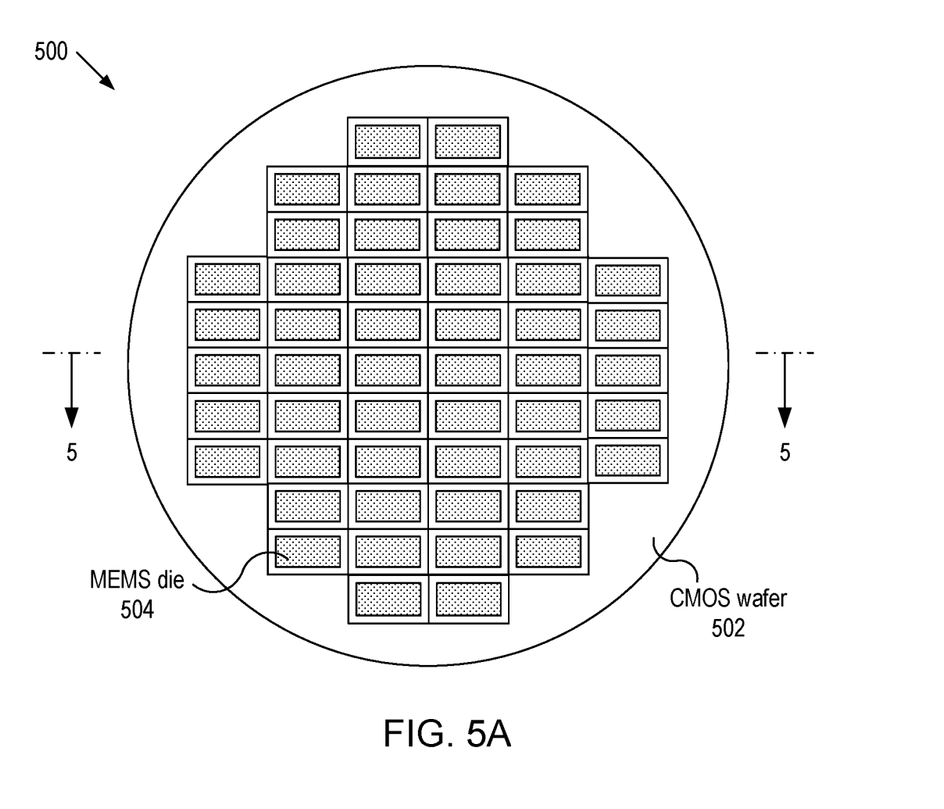
FIG. 5A shows a top view of a flip-chip assembled pMUT dice on a CMOS wafer according to embodiments of the present disclosure.
Figure 5B:
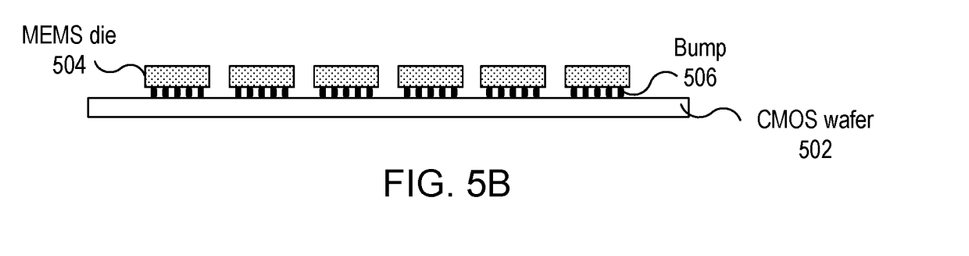
FIG. 5B shows a cross sectional view of the flip-chip assembly in FIG. 5, taken along the direction 5-5, according to embodiments of the present disclosure.

FIG. 5A shows a top view of a flip-chip assembly 500 that includes multiple MEMS dice (or a MEMS wafer) 504 mounted on a CMOS wafer 502 according to embodiments of the present disclosure. FIG. 5B shows a cross sectional view of the flip-chip assembly 500, taken along the direction 5-5, according to embodiments of the present disclosure. As depicted, the MEMS dice 504 may be mounted on the CMOS wafer 502 by metal bumps or pillars 506. In embodiments, the CMOS wafer 502 may include ASIC for controlling the pMUTs in the MEMS dice 504. (Hereinafter, the terms CMOS and ASIC are used interchangeably.) In embodiments, the pitch between bumps or pillars 506 may range 1-100 micrometer, enabling a high density interconnects applicable to the MEMS dice having a large array of pMUTs. In embodiments, the MEMS dice 504 with large number of pMUTs may be used for two-, three-, and four-dimensional imaging.

Figure 6:
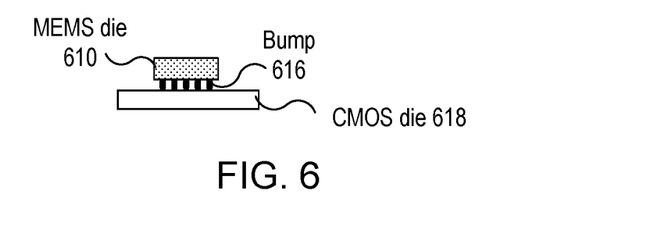
FIG. 6 shows a cross sectional view of the singulated flip-chip assembly that includes a MEMS die and a CMOS die according to embodiments of the present disclosure.

FIG. 6 shows a cross sectional view of a singulated flip-chip assembly that includes a MEMS die 610 mounted on a CMOS die 618 according to embodiments of the present disclosure. In embodiments, the MEMS die 610 may be similar to the MEMS die 504. In embodiments, a MEMS wafer having multiple MEMS dice may be fabricated and diced into single chips. Similarly, in embodiments, a CMOS wafer having multiple ASIC chips may be fabricated and diced into single chips. Then, as depicted in FIG. 6, a MEMS die 610 may be mounted on a CMOS die 618 by multiple bumps or pillars 616.

In embodiments, a single MEMS die may be mounted on the CMOS wafer. In embodiments, the flip-chip assembly may be created by die-on-die, die-on-wafer, or wafer-on-wafer bonding. In embodiments, a wafer-to-wafer bonding process may result in the yield multiplication effect, i.e., the integrated (assembled) die yield may be a product of the MEMS wafer yield multiplied by CMOS wafer yield. In embodiments, a good known die-on-die bonding process or a good known die on good known wafer site bonding process may eliminate the yield multiplication effect.

Figure 7:
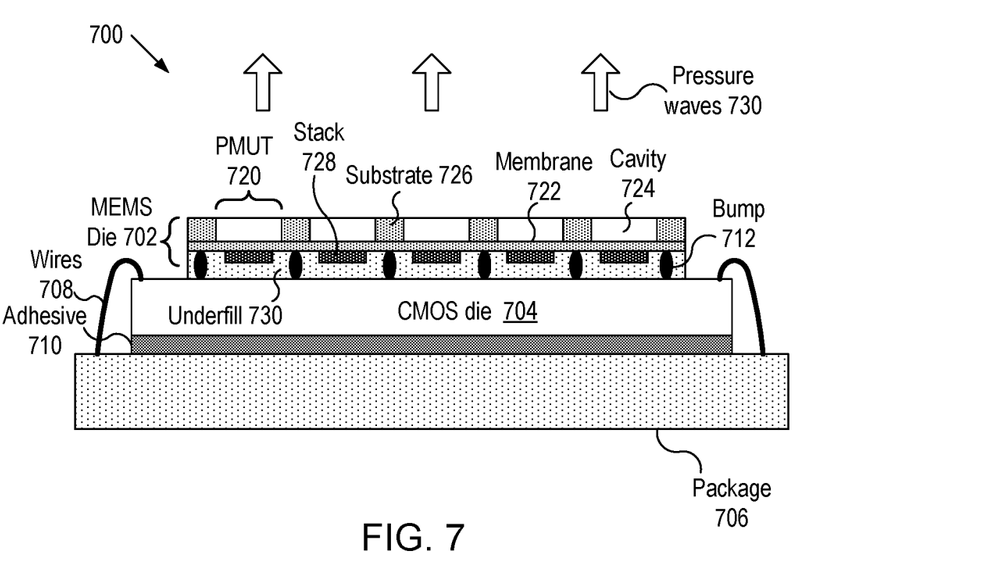
FIG. 7 shows a cross sectional view of a MEMS-CMOS assembly according to embodiments of the present disclosure.

FIG. 7 shows a cross sectional view of a MEMS-CMOS assembly 700 according to embodiments of the present disclosure. As depicted, the MEMS-CMOS assembly 700 may include: a MEMS die 702; a CMOS die 704 electrically coupled to the MEMS die by bump or pillars 712; and a package 706 secured to the CMOS die by an adhesive layer 710. In embodiments, the CMOS die 704 may be electrically coupled to the package 706 by one or more wires 708. In embodiments, the tips of each wire 708 may be coupled to the CMOS die 704 and package 706 by a wire bonding technique.

In embodiments, the MEMS die 702, which may be similar to the MEMS die 300 in FIG. 3, may include an array of pMUTs 720, where each pMUT may be similar to the pMUT 400 in FIG. 4. In embodiments, each pMUT 720 may include a membrane 722 formed on a substrate 726 and a stack of layers 728 that include a bottom electrode, a piezoelectric layer, and one or more top electrodes. In embodiments, the membrane 722 may be formed by etching a cavity in the substrate 726, i.e., a monolithic body may be etched to form a cavity so that the non-etched portion becomes the substrate and the etched portion defines the membrane. In alternative embodiments, the membrane 722 may be formed of different material than the substrate 726. In embodiments, the MEMS die 702 may include one or more membranes 722.

In embodiments, portions of the MEMS die 702 may be directly attached to the bumps 712 to provide electrical connection to CMOS die 704. In embodiments, at least one metal layer may be deposited on the bottom surface of the MEMS die and patterned to thereby form electrical connections (such as wires and/or traces), where some of the electrical connections may be in direct contact with the bumps 712 for electrical communication with the CMOS die 704. For instance, a conductor, which may be similar to the conductor (O) 404, may be an electrical wire (or trace) formed by depositing and patterning a metal layer on the bottom surface of the MEMS die 702.

If the MEMS-CMOS assembly 700 inadvertently falls on a hard surface, the impact may generate a shock in the order of 10,000 g, which may shear the bumps or pillars 712. In embodiments, the space between the MEMS die 702 and the CMOS die 704 may be filled with underfill material 730 that may reduce the external stress impact and protect the components, such as bumps 712, that are sensitive to impact stress. Also, the underfill material (layer) 730 may mechanically secure the MEMS die 702 to the CMOS die 704. In embodiments, the underfill material 730 may additionally have acoustic damping properties to absorb the pressure wave that passes through the underfill material 730.

In embodiments, the pMUTs 720 may be electrically coupled to the bumps or pillars 712 by suitable electrical conductors (such as 404, 408 and 414). In embodiments, the electrical connections may include metal traces (and vias) formed on the bottom surface of the membrane 722 and on the stack of layers 728.

In embodiments, the CMOS die 704 may include electrical circuits for sensing and driving the pMUTs 720 so that the pMUTs may generate pressure waves during the transmit mode/process and develop electrical charge during the receive mode/process. During the transmit mode, the driving circuit in the CMOS die 704 may send electrical pulses to the pMUTs 720 via the bumps 712 and, in response to the pulses, the pMUTs may vibrate the membrane 722 in the vertical direction to generate pressure waves 730. During the receive mode, the pressure waves reflected from the target organ may deform the membrane 722, which in turn develop electrical charges in the pMUTs 720. The electrical charges may be sent to the electrical circuits in the CMOS die 704 via the bumps 712 for further processing.

During the transmit mode, a portion of the pressure waves generated by the membrane 722 may propagate toward the CMOS die 704. Since these pressure waves may be reflected from the CMOS die 704 and/or package 706 to interfere with the pressure waves reflected from the target organ, these pressure waves may negatively affect the image quality. In embodiments, the adhesive material 730 may be formed of acoustic damping material that may absorb the undesirable pressure waves and dissipate into heat energy.

In embodiments, the package 706 may connect electrical signals to/from the CMOS die 704 by one or more wires 708. In embodiments, the ASIC site of the CMOS die 704 may be somewhat larger than MEMS die 704 to enable wire bonding between the ASIC site and package 706.

As discussed above, the pressure waves propagating toward the package 706 may be undesirable since they may be reflected from the package 706 and interfere with the pressure waves reflected from the target organ. In embodiments, the adhesive layer 710 may be formed of acoustic damping material so that the pressure waves passing through the adhesive layer 710 may be absorbed and dissipated into heat energy.

Figure 8:
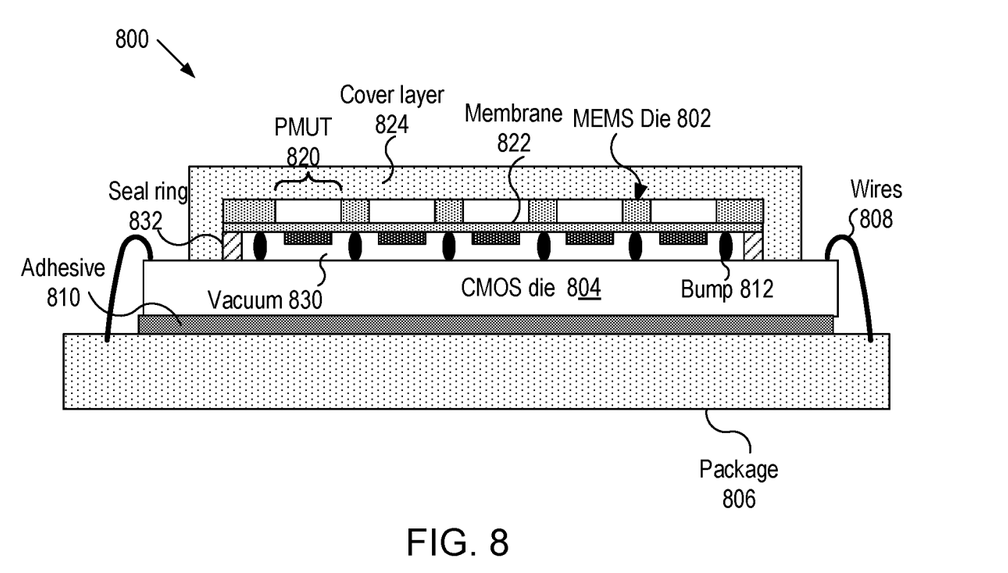
FIG. 8 shows a cross sectional view of a MEMS-CMOS assembly according to embodiments of the present disclosure.

FIG. 8 shows a cross sectional view of a MEMS-CMOS assembly 800 according to embodiments of the present disclosure. As depicted, the MEMS-CMOS assembly 800 may include: a MEMS die 802; a CMOS die 804 electrically coupled to the MEMS die by bump or pillars 812; a package 806 secured to the CMOS die 804 by an adhesive layer 810; and one or more wires 808 that may electrically couple the package 806 to the CMOS die 804. In embodiments, the MEMS die 802, CMOS die 804, and the package 806 may be similar structures and functions as their counterparts in the MEMS-CMOS assembly 700.

As discussed in conjunction with FIG. 7, the membrane 822 may generate pressure waves during the transmit mode, and a portion of the pressure wave may propagate toward the CMOS die 804. To reduce (or remove) the intensity of this undesirable pressure waves, the MEMS-CMOS assembly 800 may include a seal ring 832 that may be disposed around the perimeter of the MEMS die 802, and the space 830 enclosed by the seal ring may be kept in vacuum or in very low pressure, reducing/blocking propagation of the pressure waves through the space. For instance, the space 830 may be filled with inert gas or air at a preset pressure, preferably lower than the atmospheric pressure.

In embodiments, the cover layer 824 may be disposed around a side of the MEMS die 802 that faces the human body. The cover layer 824 may function as an impedance matching layer between the MEMS die 802 and the human body to enhance the acoustic impedance matching at the interface and also as a protection mechanism provides protection against external impact/shock, and prevents the MEMS die from directly touching the human skin to thereby provide protection against wear and tear.

Figure 9:
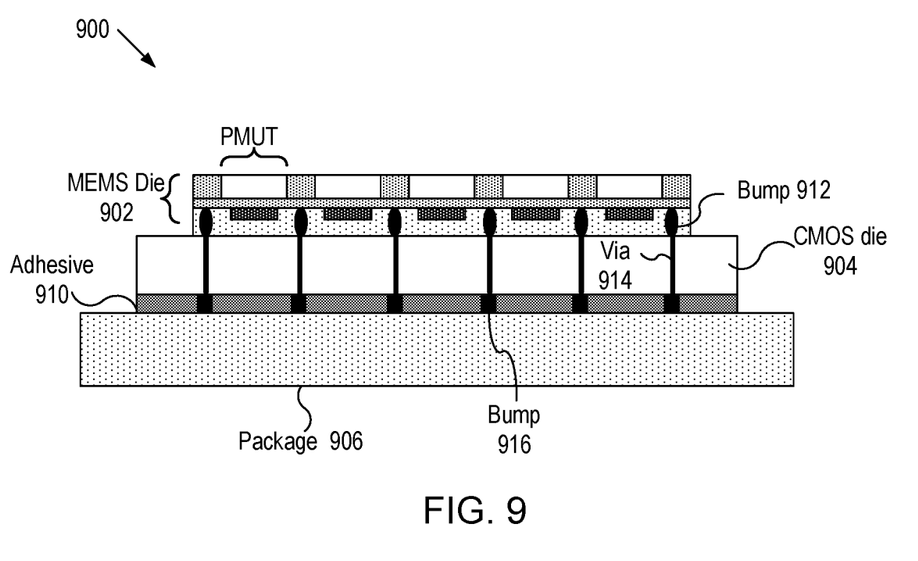
FIG. 9 shows a cross sectional view of a MEMS-CMOS assembly according to embodiments of the present disclosure.

FIG. 9 shows a cross sectional view of a MEMS-CMOS assembly 900 according to embodiments of the present disclosure. As depicted, the MEMS-CMOS assembly 900 is similar to the MEMS assembly 700, with the difference that the CMOS die 904 may be electrically coupled to the package 906 by through-vias (TVS) 914 and bumps or pillars 916. In embodiments, the TVS 914 may be formed in the CMOS die 904 by suitable wafer processing techniques, such as etching through holes and depositing/filling the holes with electrically conducting material. In embodiments, the additional bumps or pillars 916 may be formed on the CMOS die 904 or package 906, providing electrical connection between CMOS die 904 and package 906. In embodiments, the package 906 may communicate electrical signals to the CMOS 904 through the TVS 914 and bumps or pillars 916. It is noted that the adhesive layer 910 may be formed of acoustic damping material so that the pressure waves may be absorbed and dissipated into heat energy.

It is noted that a cover layer, which is similar to the cover layer 824, may be disposed around the MEMS die 902, as shown in FIG. 8. Also, it is noted that the MEMS assembly 900 may include a seal ring, which is similar to the seal ring 832, so that the space enclosed by the seal ring may be kept in vacuum to prevent the pressure waves from propagating toward the CMOS die 904. Also, in embodiments, the space between the MEMS die 902 and the CMOS 904 die may be filed with an underfill material that is similar to the material 730.

Figure 10:
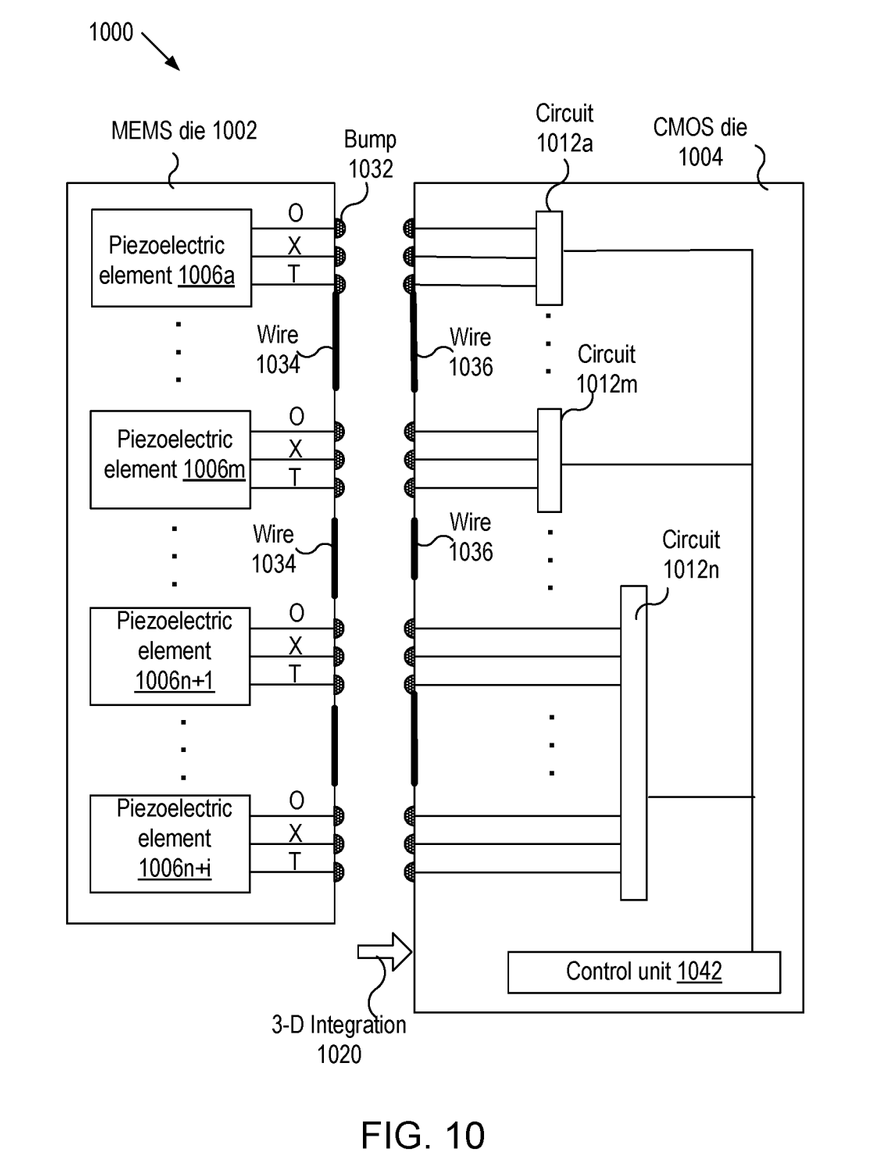
FIG. 10 shows an exemplary schematic diagram of a MEMS-CMOS assembly according to embodiments of the present disclosure.

FIG. 10 shows an exemplary schematic diagram of a MEMS-CMOS assembly (or shortly assembly) 1000 according to embodiments of the present disclosure. In embodiments, the MEMS die 1002 and CMOS die (or ASIC chip) 1004 may be similar to the MEMS die 702 (802 and 902) and CMOS die 704 (804 and 904), respectively. In the conventional systems, the electronics for driving piezoelectric transducers is typically located far away from the piezoelectric transducers and are connected to the piezoelectric transducers using a coax cable. In general, the coax cable increases parasitic loading, such as additional capacitance, on the electronics, and the additional capacitance causes more heat and loss of electrical power. In contrast, as depicted in FIG. 10, the transmit driver or drivers (or equivalently circuits) 1012a-1012n (or collectively 1012) may be connected directly to piezoelectric elements (or equivalently pixels) 1006a-1006n+i (or collectively 1006) using a low impedance two dimensional (2D) interconnect mechanism (as indicated by an arrow 1020), such as Cu pillars or solder bumps 1032 (which may be similar to the bumps 712, 812, or 912), or wafer bonding or similar approaches. In embodiments, upon integrating the MEMS die 1002 to the CMOS die 1004, the circuits 1012 may be located less than 100 μm vertically (or so) away from the piezoelectric elements 1006. In embodiments, any conventional device for impedance matching between driver circuits 1012 and piezoelectric elements 1006 may not be required, further simplifying design and increasing power efficiency of the assembly 1000. Impedance of the circuits 1012 may be designed to match the requirement of the piezoelectric elements 1006.

It is noted that each piezoelectric element may be coupled to a corresponding driving circuit by more than three bumps if the piezoelectric element has more than two top electrodes. Furthermore, as discussed below, each piezoelectric element may be coupled to a corresponding driving circuit by less than three bumps. Thus, it should be apparent to those of ordinary skill in the art that FIG. 10 shows an exemplary connection mechanism between a MEMS die and a CMOS die.

In embodiments, each of the piezoelectric elements 1006 may have three leads represented by X, T, and O. The leads from each of the piezoelectric elements may be electrically connected to a corresponding one of the circuits 1012 located in the CMOS die 1004 by the bumps 1032. In embodiments, a line of piezoelectric elements, such as 1006n+1-1006n+i may be electrically coupled to one common circuit 1012n. In embodiments, the transmit driver circuit 1012n may include one transmit driver that generates transmit signals to the piezoelectric elements during the transmit mode. In alternative embodiment, connecting traces on MEMS or ASIC may be fabricate using thick metal, e.g., 10 μm, instead typical metallization on the order of 1 μm.

It should be apparent to those of ordinary skill in the art that the CMOS die 1004 may have any suitable number of circuits that are similar to the circuit 1012n. In embodiments, the control unit 1042 may have capability to configure the piezoelectric elements, either horizontally or vertically in a two dimensional pixel array, configure their length and put them into transmit or receive or poling mode or idle mode. In embodiments, the control unit 1042 may perform the poling process after the MEMS die 1002 is combined with the CMOS die 1004 by the bumps 1032. More information on the assembly 1000 may be found in a copending U.S. patent application Ser. No. 15/826,606, entitled "CON-FIGURABLE ULTRASONIC IMAGER," filed on Nov. 29, 2017, which is herein incorporated by reference in its entirety.

In embodiments, at least one metal layer may be deposited on a surface of the MEMS die 1002 and patterned to thereby form electrical wires (or traces) 1034, where some of the electrical wires may be in direct contact with the bumps 1032 for electrical communication with the CMOS die 1004. The electrical wires 1034 may be also used to communicate signals between the piezoelectric elements 1006. In embodiments, at least one metal layer may be deposited on a surface of the CMOS die 1004 and patterned to thereby form electrical wires (or traces) 1036, where some of the electrical wires may be in direct contact with the bumps 1032 for electrical communication with the MEMS die 1002. The electrical wires 1036 may be also used to communicate signals between the electrical components in the CMOS die 1004. In embodiments, multiple metal layers and vias may be deposited and patterned on the MEMS ide and/or CMOS die to form multiple layers of electrical wires (traces).

As discussed in conjunction with FIGS. 7-9, in embodiments, the MEMS die 1002 and CMOS die 1004 may be manufactured separately and combined to each other by a 2D interconnect technology, such as metal interconnect technology using bumps 1032. In embodiments, the interconnect technology may eliminate the low yield multiplication effect of wafer to wafer integration, lowering the yield of components. In embodiments, the MEMS die in FIG. 10 may have similar structures and functions as the MEMS die in FIGS. 7-9, and the CMOS die in FIG. 10 may have similar structures and functions as the MEMS die in FIGS. 7-9.

Figure 11A:
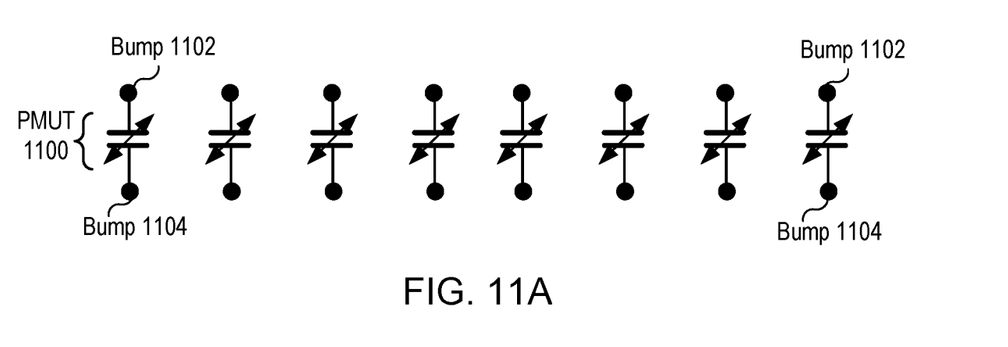
FIG. 11A shows a schematic diagram of electrical connections of pMUTs according to embodiments of the present disclosure.

FIG. 11A shows a schematic diagram of electrical connections of pMUTs 1100 according to embodiments of the present disclosure. As depicted, each pMUT 1100 may be symbolically represented by a capacitor having top and bottom electrodes. In embodiments, the top of each pMUT 1100 may be electrically coupled to a bump 1102 and the bottom electrode of each pMUT may be electrically coupled to a bump 1104, where the bumps 1102 and 1104 may be similar to the bumps 712, 812, 912, and 1082.

Figure 11B:
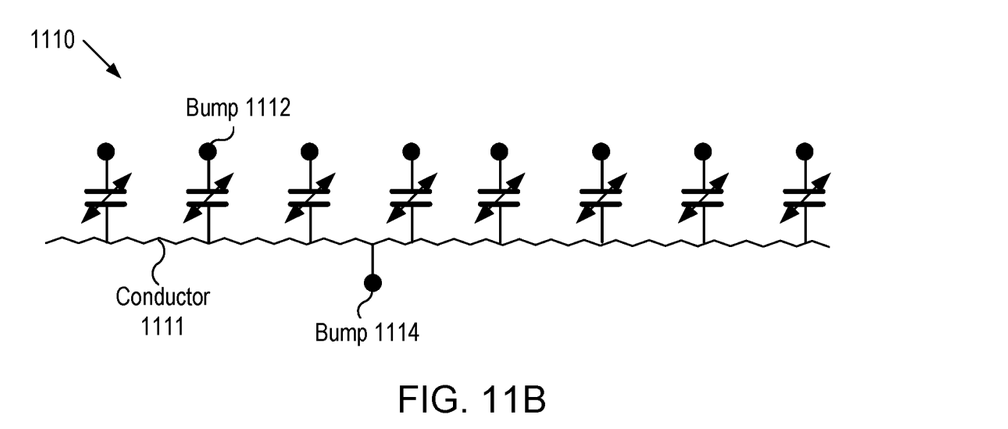
FIG. 11B shows a schematic diagram of electrical connections of pMUTs according to embodiments of the present disclosure.

Since each electrode is directly coupled to one bump, the drive circuit resistance is the smallest, but the number of interconnections (bumps) is the highest, potentially impacting the bumping yield as the number of pMUTs in the MEMS die increases. To optimize the number of bumps and the drive circuit resistance, some bumps or pillars may be shared by multiple pMUTs. In embodiments, a thick metal layer may be deposited on at least one of the MEMS die and CMOS die and two or more electrodes in the pMUTs may be electrically coupled to the thick metal layer. FIG. 11B shows a schematic diagram of electrical connections of pMUTs according to embodiments of the present disclosure. As depicted, the top electrode of each pMUT may be electrically coupled to a bump 1112, while the bottom electrodes of the eight pMUTs in the array 1110 may be electrically coupled to a bump 1114 via a common conductor 1111.

In embodiments, the conductor 1111 may be formed by depositing a thick metal layer on the CMOS die (and/or on the MEMS die) and patterning the metal layer. More specifically, a thick metal layer may be formed on the top surface of the CMOS die 1004 (and/or on the bottom surface of the MEMS die 1002) and patterned by a suitable wafer processing technique to form electrical wires/traces 1036 (and/or 1034), where some of the wires 1036 (and/or 1034) may be used as the conductor 1111. During operation, the current flowing through the conductor 1111 may be in the order of one Ampere. As such, the resistivity of the wire 1036 (and/or 1034) needs to be very low, and to reduce the resistivity of the wire, the thickness of the metal layer may be adjusted. In embodiments, the thickness of the metal layer may be about 10 µm. Compared to the connection arrangement in FIG. 11A, the conductor 1111 may reduce the number of bumps required for the electrical connection of the bottom electrodes to a CMOS die.

Figure 11C:
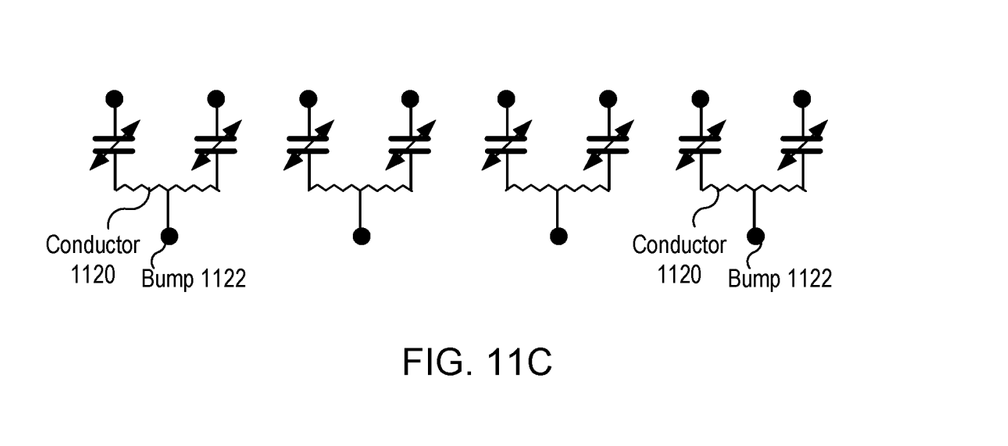
FIG. 11C shows a schematic diagram of electrical connections of pMUTs according to embodiments of the present disclosure.

Even though the electrical connections in FIG. 11B require smaller number of bumps than the electrical connections in FIG. 11A, different pMUTs in the array 1110 may have different series resistances, resulting in different drive voltages at the pMUTs during the transmit mode. As the pMUTs may be driven by pulses having high spike currents during the transmit mode, the different drive voltages may reduce the operational efficiency of the pMUT array 1110 and possibly degrade the image quality. To reduce the number of bumps without compromising the series resistance significantly, the number of pMUTs coupled to a common conductor may be adjusted. FIG. 11C shows a schematic diagram of electrical connections of pMUTs according to embodiments of the present disclosure. In embodiments, two bottom electrodes of two pMUTs in the MEMS die may be electrically coupled to a common electrical conductor 1120, which in turn may be electrically coupled to a bump 1122.

In embodiments, by way of example, each pMUT in FIG. 11B may have one bottom electrode and one top electrode. In such a configuration, the top electrode of each pMUT may be coupled to a separate bump and the two bottom electrodes of the two adjacent pMUTs may be coupled to one bump via the conductor 1120, i.e., only three bumps are needed to couple two pMUTs to a CMOS die. Stated differently, the number of interconnects (i.e., bumps) may be equal to 1.5 times the number of pMUTs, but the series resistance may be increased only by a factor of 2, compared to the configuration in FIG. 11A.

It is noted that other suitable number of pMUTs may be electrically coupled to a common conductor. For instance, each pMUT may include one bottom electrode and one top electrode, and the top electrode of each pMUT may be coupled to a separate bump while the four bottom electrodes of four adjacent pMUTs may be coupled to a common conductor. In such a case, only five bumps are needed to electrically connect four pMUTs to a CMOS die, i.e., the number of interconnects (i.e., bumps) may be equal to 1.25 times the number of pMUTs.

It is noted that, as shown in FIG. 4, each pMUT may have two or more top electrodes (such as 406 and 412). In such a case, to reduce the number of bumps, two or more X electrodes of adjacent pMUTs may be coupled to a first common electrode while two or more T electrodes of adjacent pMUTs may be coupled to a second common electrode.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A transducer assembly, comprising:
   a microelectromechanical systems (MEMS) die including a plurality of piezoelectric elements;
   a complementary metal-oxide-semiconductor (CMOS) die electrically coupled to the MEMS die by a first plurality of bumps and including at least one circuit for controlling the plurality of piezoelectric elements;
   a seal ring disposed around a perimeter of the MEMS die and between the MEMS die and the CMOS die to thereby define an enclosed space, wherein the enclosed space is in vacuum; and
   a package secured to the CMOS die by an adhesive layer and electrically connected to the CMOS die.

2. The transducer assembly of claim 1, wherein each of the plurality of piezoelectric elements includes:
   a substrate;
   a membrane disposed on the substrate; and
   a stack of layers disposed on at least one of the membrane and substrate and having a bottom electrode, a piezoelectric layer and a top electrode.

3. The transducer assembly of claim 2, further comprising: a plurality of electrical wires formed on the MEMS die, wherein at least one electrical wire of the plurality of electrical wires is in direct contact with the first plurality of bumps.

4. The transducer assembly of claim 2, further comprising: a cover layer for covering the substrates of the plurality of piezoelectric elements and formed of an impedance matching material.

5. The transducer assembly of claim 2, wherein the substrate includes a cavity and a portion of the substrate thinned by the cavity corresponds to the membrane and wherein the stack of layers vibrates the membrane to generate a pressure wave that propagates from the membrane.

6. The transducer assembly of claim 1, wherein the adhesive layer is formed of acoustic damping material for absorbing a pressure wave that passes through the adhesive layer.

7. The transducer assembly of claim 1, further comprising: at least one wire having one end connected to the CMOS die and another end connected to the package, wherein the CMOS die electrically communicates with the package via the at least one wire.

8. The transducer assembly of claim 1, further comprising: a conductor electrically coupled to two or more top electrodes of the plurality of piezoelectric elements, wherein a bottom electrode of each of the plurality of piezoelectric elements is electrically coupled to one bump of the first plurality of bumps and wherein the conductor is electrically coupled to another bump of the first plurality of bumps.

9. The transducer assembly of claim 1, wherein a top electrode of two or more of the plurality of piezoelectric elements is electrically coupled to one bump of the first plurality of bumps and a bottom electrode of each of the plurality of piezoelectric elements is electrically coupled to another bump of the first plurality of bumps.

10. The transducer assembly of claim 1, further comprising: a metal layer formed on at least one of the MEMS die and CMOS die and patterned to form one or more electrical connections.

11. An imaging device, comprising:
    a transducer assembly, including:
      a microelectromechanical systems (MEMS) die including a plurality of piezoelectric elements;
      a complementary metal-oxide-semiconductor (CMOS) die electrically coupled to the MEMS die by a first plurality of bumps and including at least one circuit for controlling the plurality of piezoelectric elements;

a seal ring disposed around a perimeter of the MEMS die and between the MEMS die and the CMOS die to thereby define an enclosed space, wherein the enclosed space is in vacuum; and a package secured to the CMOS die by an adhesive layer and electrically connected to the CMOS die;

a processor for processing signals from the transducer assembly; and a display for displaying an image based on signals processed by the processor.

12. The imaging device of claim 11, wherein each of the plurality of piezoelectric elements includes:
a substrate;
a membrane disposed on the substrate; and
a stack of layers disposed on at least one of the membrane and substrate and having a bottom electrode, a piezoelectric layer and a top electrode.

13. The imaging device of claim 12, further comprising: a cover layer for covering the substrates of the plurality of piezoelectric elements and formed of impedance matching material that increases transmission of a pressure wave generated by the plurality of piezoelectric elements.

14. The imaging device of claim 12, wherein the substrate includes a cavity and a portion of the substrate thinned by the cavity corresponds to the membrane.

15. The imaging device of claim 11, wherein the adhesive layer is formed of acoustic damping material for absorbing a pressure wave generated by the plurality of piezoelectric elements.

16. The imaging device of claim 11, further comprising: at least one wire having one end connected to the CMOS die and another end connected to the package, wherein the CMOS die electrically communicates with the package via the at least one wire.

17. The imaging device of claim 11, further comprising: a metal layer formed on at least one of the MEMS die and CMOS die and patterned to form one or more electrical connections.

18. A transducer assembly, comprising:
a microelectromechanical systems (MEMS) die including a plurality of piezoelectric elements;
a complementary metal-oxide-semiconductor (CMOS) die electrically coupled to the MEMS die by a first plurality of bumps and including at least one circuit for controlling the plurality of piezoelectric elements;
a seal ring disposed around a perimeter of the MEMS die and between the MEMS die and the CMOS die to thereby define an enclosed space, wherein the enclosed space is filled with at least one of inert gas and air; and
a package secured to the CMOS die by an adhesive layer and electrically connected to the CMOS die.

19. The transducer assembly of claim 18, wherein each of the plurality of piezoelectric elements includes:
a substrate;
a membrane disposed on the substrate; and
a stack of layers disposed on at least one of the membrane and substrate and having a bottom electrode, a piezoelectric layer and a top electrode.

20. The transducer assembly of claim 19, further comprising: a plurality of electrical wires formed on the MEMS die, wherein at least one electrical wire of the plurality of electrical wires is in direct contact with the first plurality of bumps.

21. The transducer assembly of claim 19, further comprising: a cover layer for covering the substrates of the plurality of piezoelectric elements and formed of an impedance matching material.

22. The transducer assembly of claim 19, wherein the substrate includes a cavity and a portion of the substrate thinned by the cavity corresponds to the membrane and wherein the stack of layers vibrates the membrane to generate a pressure wave that propagates from the membrane.

23. The transducer assembly of claim 18, wherein the adhesive layer is formed of acoustic damping material for absorbing a pressure wave that passes through the adhesive layer.

24. The transducer assembly of claim 18, further comprising: at least one wire having one end connected to the CMOS die and another end connected to the package, wherein the CMOS die electrically communicates with the package via the at least one wire.

25. The transducer assembly of claim 18, further comprising: a conductor electrically coupled to two or more top electrodes of the plurality of piezoelectric elements, wherein a bottom electrode of each of the plurality of piezoelectric elements is electrically coupled to one bump of the first plurality of bumps and wherein the conductor is electrically coupled to another bump of the first plurality of bumps.

26. The transducer assembly of claim 18, wherein a top electrode of two or more of the plurality of piezoelectric elements is electrically coupled to one bump of the first plurality of bumps and a bottom electrode of each of the plurality of piezoelectric elements is electrically coupled to another bump of the first plurality of bumps.

27. The transducer assembly of claim 18, further comprising: a metal layer formed on at least one of the MEMS die and CMOS die and patterned to form one or more electrical connections.

28. An imaging device, comprising:
a transducer assembly, including:
a microelectromechanical systems (MEMS) die including a plurality of piezoelectric elements;
a complementary metal-oxide-semiconductor (CMOS) die electrically coupled to the MEMS die by a first plurality of bumps and including at least one circuit for controlling the plurality of piezoelectric elements;
a seal ring disposed around a perimeter of the MEMS die and between the MEMS die and the CMOS die to thereby define an enclosed space, wherein the enclosed space is filled with at least one of inert gas and air; and
a package secured to the CMOS die by an adhesive layer and electrically connected to the CMOS die;
a processor for processing signals from the transducer assembly; and
a display for displaying an image based on signals processed by the processor.

29. The imaging device of claim 28, wherein each of the plurality of piezoelectric elements includes:
a substrate;
a membrane disposed on the substrate; and
a stack of layers disposed on at least one of the membrane and substrate and having a bottom electrode, a piezoelectric layer and a top electrode.

30. The imaging device of claim 29, further comprising: a cover layer for covering the substrates of the plurality of piezoelectric elements and formed of impedance matching material that increases transmission of a pressure wave generated by the plurality of piezoelectric elements.

31. The imaging device of claim 29, wherein the substrate includes a cavity and a portion of the substrate thinned by the cavity corresponds to the membrane.

32. The imaging device of claim 28, wherein the adhesive layer is formed of acoustic damping material for absorbing a pressure wave generated by the plurality of piezoelectric elements.

33. The imaging device of claim 28, further comprising: at least one wire having one end connected to the CMOS die and another end connected to the package, wherein the CMOS die electrically communicates with the package via the at least one wire.

34. The imaging device of claim 28, further comprising: a metal layer formed on at least one of the MEMS die and CMOS die and patterned to form one or more electrical connections.

35. A transducer assembly, comprising:
a microelectromechanical systems (MEMS) die including a plurality of piezoelectric elements;
a complementary metal-oxide-semiconductor (CMOS) die electrically coupled to the MEMS die by a first plurality of bumps and including at least one circuit for controlling the plurality of piezoelectric elements;
a package secured to the CMOS die by an adhesive layer and electrically connected to the CMOS die; and
a second plurality of bumps formed in the adhesive layer, wherein the CMOS die includes a plurality of through silicon vias (TSV) and the first plurality of bumps are electrically coupled to the second plurality of bumps by the plurality of through silicon vias.

36. The transducer assembly of claim 35, wherein each of the plurality of piezoelectric elements includes:
a substrate;
a membrane disposed on the substrate; and
a stack of layers disposed on at least one of the membrane and substrate and having a bottom electrode, a piezoelectric layer and a top electrode.

37. The transducer assembly of claim 36, further comprising: a plurality of electrical wires formed on the MEMS die, wherein at least one electrical wire of the plurality of electrical wires is in direct contact with the first plurality of bumps.

38. The transducer assembly of claim 36, further comprising: a cover layer for covering the substrates of the plurality of piezoelectric elements and formed of an impedance matching material.

39. The transducer assembly of claim 36, wherein the substrate includes a cavity and a portion of the substrate thinned by the cavity corresponds to the membrane and wherein the stack of layers vibrates the membrane to generate a pressure wave that propagates from the membrane.

40. The transducer assembly of claim 35, wherein the adhesive layer is formed of acoustic damping material for absorbing a pressure wave that passes through the adhesive layer.

41. The transducer assembly of claim 35, further comprising: an underfill layer disposed between the MEMS die and CMOS die and mechanically securing the MEMS die to the CMOS die.

42. The transducer assembly of claim 41, wherein the underfill layer is formed of a material that absorbs a pressure wave that passes through the material.

43. The transducer assembly of claim 35, further comprising: a layer formed of underfill material and disposed between the MEMS die and the CMOS die and securing the MEMS die to the CMOS die, wherein the underfill material includes acoustic damping material for absorbing a pressure wave that passes through the underfill material.

44. The transducer assembly of claim 35, further comprising: at least one wire having one end connected to the CMOS die and another end connected to the package, wherein the CMOS die electrically communicates with the package via the at least one wire.

45. The transducer assembly of claim 35, further comprising: a conductor electrically coupled to two or more top electrodes of the plurality of piezoelectric elements, wherein a bottom electrode of each of the plurality of piezoelectric elements is electrically coupled to one bump of the first plurality of bumps and wherein the conductor is electrically coupled to another bump of the first plurality of bumps.

46. The transducer assembly of claim 35, wherein a top electrode of two or more of the plurality of piezoelectric elements is electrically coupled to one bump of the first plurality of bumps and a bottom electrode of each of the plurality of piezoelectric elements is electrically coupled to another bump of the first plurality of bumps.

47. The transducer assembly of claim 35, further comprising: a metal layer formed on at least one of the MEMS die and CMOS die and patterned to form one or more electrical connections.

48. An imaging device, comprising:
a transducer assembly, including:
a microelectromechanical systems (MEMS) die including a plurality of piezoelectric elements;
a complementary metal-oxide-semiconductor (CMOS) die electrically coupled to the MEMS die by a first plurality of bumps and including at least one circuit for controlling the plurality of piezoelectric elements;
a package secured to the CMOS die by an adhesive layer and electrically connected to the CMOS die; and
a second plurality of bumps formed in the adhesive layer, wherein the CMOS die includes a plurality of through vias and the first plurality of bumps are electrically coupled to the second plurality of bumps by the plurality of through vias;
a processor for processing signals from the transducer assembly; and
a display for displaying an image based on signals processed by the processor.

49. The imaging device of claim 48, wherein each of the plurality of piezoelectric elements includes: a substrate; a membrane disposed on the substrate; and a stack of layers disposed on at least one of the membrane and substrate and having a bottom electrode, a piezoelectric layer and a top electrode.

50. The imaging device of claim 49, further comprising: a cover layer for covering the substrates of the plurality of piezoelectric elements and formed of impedance matching material that increases transmission of a pressure wave generated by the plurality of piezoelectric elements.

51. The imaging device of claim 49, wherein the substrate includes a cavity and a portion of the substrate thinned by the cavity corresponds to the membrane.

52. The imaging device of claim 48, wherein the adhesive layer is formed of acoustic damping material for absorbing a pressure wave generated by the plurality of piezoelectric elements.

53. The imaging device of claim 48, further comprising: an underfill layer disposed between the MEMS die and CMOS die and mechanically securing the MEMS die to the CMOS die.

54. The imaging device of claim 53, wherein the underfill layer is formed of a material that absorbs a pressure wave that passes through the material.

55. The imaging device of claim 48, further comprising: a layer formed of underfill material and disposed between the MEMS die and the CMOS die and securing the MEMS die to the CMOS die, wherein the underfill material includes acoustic damping material for absorbing a pressure wave that passes through the underfill material.

56. The imaging device of claim 48, further comprising: at least one wire having one end connected to the CMOS die and another end connected to the package, wherein the CMOS die electrically communicates with the package via the at least one wire.

57. The imaging device of claim 48, further comprising: a metal layer formed on at least one of the MEMS die and CMOS die and patterned to form one or more electrical connections.

\* \* \* \* \*